US008968576B2

(12) United States Patent
Holland et al.

(10) Patent No.: US 8,968,576 B2
(45) Date of Patent: Mar. 3, 2015

(54) NEBULIZING TREATMENT METHOD

(75) Inventors: Jennifer E. Holland, Richland, WA (US); Robert S. Reimers, Metairie, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 2004 days.

(21) Appl. No.: 11/292,328

(22) Filed: Nov. 30, 2005

(65) Prior Publication Data

US 2007/0221582 A1 Sep. 27, 2007

Related U.S. Application Data

(60) Provisional application No. 60/631,781, filed on Nov. 30, 2004.

(51) Int. Cl.
*C02F 1/32* (2006.01)
*C02F 1/72* (2006.01)
(Continued)

(52) U.S. Cl.
CPC .................. *C02F 1/72* (2013.01); *A61M 15/02* (2013.01); *B01D 53/8687* (2013.01); *B01D 53/90* (2013.01); *C02F 1/30* (2013.01); *C02F 1/36* (2013.01); *A61M 2205/3317* (2013.01); *B01D 2251/102* (2013.01); *B01D 2251/104* (2013.01); *B01D 2255/207* (2013.01); *B01D 2255/20707* (2013.01); *B01D 2255/20753* (2013.01); *B01D 2255/20776* (2013.01);
(Continued)

(58) Field of Classification Search
USPC ............ 210/669, 683, 749, 600, 748, 748.01, 210/253, 758, 748.02, 748.03, 748.1, 210/748.08; 435/173.1; 239/128; 422/20, 422/21
See application file for complete search history.

(56) References Cited

U.S. PATENT DOCUMENTS 4,265,747 A 5/1981 Copa et al.
4,267,976 A 5/1981 Chatwin
(Continued)

FOREIGN PATENT DOCUMENTS

WO WO 9301891 A1 * 2/1993

*Primary Examiner* — Walter D Griffin
*Assistant Examiner* — Cameron J Allen
(74) *Attorney, Agent, or Firm* — Garvey, Smith, Nehrbass & North, L.L.C.; Charles C. Garvey, Jr.; Seth M. Nehrbass

(57) ABSTRACT

A method of treating contaminated air, gas and surfaces is accomplished through the nebulization of gas and/or liquid oxidants through a field of electromagnetic radiation or sonic waves. The contaminated gas and/or liquid streams are blended with gaseous and/or liquid oxidants by the nebulizer and directly injected in the energy field. Free radicals produced from oxidants in the presence of the energy field instantaneously oxidize a large effective surface area of the contaminated media. Surfaces are treated more efficiently with the energy field situated directly above and parallel to but not on the surface; a high-frequency energy field may be used to create a large concentration of free radicals without damaging the surface in a collimated beam of the field situated parallel to the surface. A catalyst may be employed at the tip (i.e. discharge orifices of gas and/or liquid) of the nebulizer or blended into the nebulized cloud to increase the formation of free radicals. The method may also be used to carry out a reduction instead of an oxidation reaction.

11 Claims, 4 Drawing Sheets

(51) Int. Cl.
*A61M 15/02* (2006.01)
*B01D 53/86* (2006.01)
*B01D 53/90* (2006.01)
*C02F 1/30* (2006.01)
*C02F 1/36* (2006.01)
*C02F 1/78* (2006.01)
*C02F 101/22* (2006.01)

(52) U.S. Cl.
CPC ............ *B01D 2255/20792* (2013.01); *B01D 2255/802* (2013.01); *B01D 2257/708* (2013.01); *B01D 2258/06* (2013.01); *B01D 2259/4508* (2013.01); *B01D 2259/804* (2013.01); *B01D 2259/806* (2013.01); *B01D 2259/81* (2013.01); *B01D 2259/812* (2013.01); *B01D 2259/816* (2013.01); *C02F 1/302* (2013.01); *C02F 1/307* (2013.01); *C02F 1/32* (2013.01); *C02F 1/722* (2013.01); *C02F 1/725* (2013.01); *C02F 1/78* (2013.01); *C02F 2101/22* (2013.01); *C02F 2303/04* (2013.01); *C02F 2305/023* (2013.01); *C02F 2305/08* (2013.01); *C02F 2305/10* (2013.01)
USPC .......... 210/748.01; 422/20; 422/21; 210/758; 210/748.02; 210/748.03; 210/748.1; 210/748.08

(56) References Cited

U.S. PATENT DOCUMENTS

| | | | |
|---|---|---|---|
| 4,344,574 A | 8/1982 | Meddings et al. | |
| 4,575,609 A | 3/1986 | Fassel et al. | |
| 4,696,719 A | 9/1987 | Bischoff | |
| 4,816,145 A | 3/1989 | Goudy, Jr. | |
| 4,849,114 A | 7/1989 | Zeff et al. | |
| 4,880,164 A * | 11/1989 | Noordermeer | 239/423 |
| 4,919,853 A * | 4/1990 | Alvarez et al. | 264/12 |
| 4,961,885 A | 10/1990 | Avrahami et al. | |
| 4,993,411 A | 2/1991 | Callaway | |
| 5,213,759 A | 5/1993 | Castberg et al. | |
| 5,246,556 A | 9/1993 | Sawamoto et al. | |
| 5,297,734 A * | 3/1994 | Toda | 239/102.2 |
| 5,364,537 A | 11/1994 | Paillard | |
| 5,366,696 A | 11/1994 | Williams | |
| 5,407,604 A | 4/1995 | Luffman | |
| 5,433,866 A | 7/1995 | Hoppe et al. | |
| 5,449,502 A | 9/1995 | Igusa et al. | |
| 5,498,374 A * | 3/1996 | Sabroske et al. | 261/77 |
| 5,512,244 A | 4/1996 | Griffiths et al. | |
| 5,554,295 A * | 9/1996 | Ban et al. | 210/668 |
| 5,688,378 A | 11/1997 | Khoe et al. | |
| 5,727,541 A | 3/1998 | Rowland | |
| 5,765,403 A | 6/1998 | Lincoln et al. | |
| 5,884,846 A | 3/1999 | Tan | |
| 5,922,247 A | 7/1999 | Shoham et al. | |
| 5,971,368 A | 10/1999 | Nelson et al. | |
| 6,009,869 A | 1/2000 | Corbeil | |
| 6,029,911 A | 2/2000 | Watanabe et al. | |
| 6,030,526 A | 2/2000 | Porter | |
| 6,032,876 A | 3/2000 | Bertsch et al. | |
| 6,051,256 A * | 4/2000 | Platz et al. | 424/489 |
| 6,126,086 A | 10/2000 | Browner et al. | |
| 6,166,379 A | 12/2000 | Montaser et al. | |
| 6,200,466 B1 | 3/2001 | Bender | |
| 6,264,899 B1 | 7/2001 | Caren et al. | |
| 6,322,756 B1 * | 11/2001 | Arno et al. | 422/171 |
| 6,328,898 B1 | 12/2001 | Akiyama et al. | |
| 6,361,697 B1 | 3/2002 | Coury et al. | |
| 6,403,245 B1 * | 6/2002 | Hunt | 429/33 |
| 6,468,433 B1 | 10/2002 | Tribelski | |
| 6,478,238 B1 | 11/2002 | Wachs et al. | |
| 6,511,050 B2 | 1/2003 | Chu | |
| 6,555,011 B1 | 4/2003 | Tribelsky et al. | |
| 6,555,835 B1 | 4/2003 | Wydeven | |
| 6,601,776 B1 * | 8/2003 | Oljaca et al. | 239/5 |
| 6,630,105 B1 | 10/2003 | O'Neill et al. | |
| 6,761,729 B2 | 7/2004 | Babaev | |
| 6,761,863 B2 | 7/2004 | Hwang et al. | |
| 6,848,633 B2 | 2/2005 | Ryser | |
| 6,866,755 B2 | 3/2005 | Monzyk et al. | |
| 7,118,852 B2 * | 10/2006 | Purdum | 435/2 |
| 2002/0033369 A1 * | 3/2002 | Bender | 210/748 |
| 2003/0194692 A1 * | 10/2003 | Purdum | 435/2 |
| 2004/0096354 A1 | 5/2004 | Nomura et al. | |
| 2007/0004839 A1 * | 1/2007 | Yamamoto et al. | 524/417 |

* cited by examiner

NEBULIZING TREATMENT METHOD

CROSS-REFERENCE TO RELATED APPLICATIONS

Priority of U.S. Provisional Patent Application Ser. No. 60/631,781, filed 30 Nov. 2004, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

This invention relates to a method of oxidatively treating gases, liquids, slurries and surfaces in which high energy oxidants are created through the nebulization of an oxidizer into an energy field. If the media requiring treatment may itself be nebulized, treatment will occur within the radiation/energy field. If the media requiring treatment is a surface or bulk slurry, the energy field is positioned directly above but not on the surface requiring treatment. This oxidation method may be employed for disinfection, purification, sterilization, destruction of organic molecules, oxidation of inorganics, oxidation of metals, and co-precipitation of metals.

2. General Background of the Invention

Free radical formation is a process that has been developed for the purification and disinfection of contaminated liquids, gases, and surfaces. The present invention is an efficient method of free radical application through instantaneous formation of free radicals through the nebulization of liquid and gas oxidants through an energy field.

The process of nebulization or atomization has per se been used in prior art for the dispersion of powders or liquids into clouds (U.S. Pat. No. 4,993,411), humidification of air or oxygen gas for inhalation (U.S. Pat. Nos. 6,511,050; 5,407,604; 4,993,411) the dispersion of fuel into a cloud for efficient combustion (U.S. Pat. Nos. 4,696,719; 4,267,976), and the saturation of a liquid with oxygen, ozone or other gas (U.S. Pat. No. 5,366,696). The dispersion of liquids, slurries or solids into nano-sized droplets or particles increases the effective surface area available for instantaneous reaction and therefore increases efficiency of processes.

Prior art nebulizers which can be used in this process include two examples shown in U.S. Pat. No. 4,344,574 (cross-flow) and U.S. Pat. No. 4,575,605 (concentric), which both atomize a liquid with a gas at high velocity.

Concentric nebulizers have evolved into models with adjustable inner capillary tubes (see for example U.S. Pat. No. 5,884,846), tips with varying geometry (see for example U.S. Pat. No. 6,032,876), direct injection high efficiency models (see for example U.S. Pat. No. 6,166,379), a supersonic nozzle nebulization apparatus (see for example U.S. Pat. No. 6,009,869), a concentric nebulizer with electrospray capability (see for example U.S. Pat. Nos. 6,478,238 and 6,126,086), and a model with parallel paths of gas (surrounding the liquid capillary) with different velocities to direct the cloud of liquid droplets in a specific direction. A combined cross-flow ultrasonic nebulizer has also been developed (see for example U.S. Pat. No. 4,961,885.)

Other apparatuses and methods for nebulizing or atomizing a liquid solution with gas have been patented including a method of thermal pressurization (U.S. Pat. No. 6,601,776), ultrasonication (U.S. Pat. Nos. 6,555,011; 5,922,247), centrifugal pressurization (U.S. Pat. No. 5,727,541) and specialty nozzles (U.S. Pat. No. 5,269,461). These prior art references support the claimed method when the atomized liquid is combined with a stream of gas moving at substantial velocity.

Prior art patents also include any process which combines an energy field and an oxidant for the treatment of gases, liquids and solids in bulk (see U.S. Pat. Nos. 6,761,863; 6,761,729; 6,555,835; 6,468,433; 6,264,899; 5,765,403; 5,688,378; 4,816,145; 4,265,747); of particular application are advanced oxidation processes which generate hydroxyl radicals (OH.) for oxidative treatment of media (see U.S. Pat. Nos. 6,780,306; 6,630,105; 6,361,697; 6,328,898; 6,264,899; 6,200,466; 6,030,526; 5,512,244; 5,364,537; 5,213,759; 4,849,114).

Liquid treatment systems include compounded reactors geometrically shaped to enhance internally applied UV energy (see U.S. Pat. No. 6,555,011); mixing oxygen, ozone and or hydrogen peroxide into the liquid and contacting the mixture with a free radical inducer (see U.S. Pat. No. 6,361,697); pulse-discharge treatment of oxygen saturated liquid (see U.S. Pat. No. 6,328,898); treatment of water with black-body radiation (see U.S. Pat. No. 6,200,466); dual annular UV reactor which respectively form ozone from dissolved oxygen and then initiate free radical formation with photolysis of titanium dioxide (see U.S. Pat. No. 6,030,526); dissolution of UV treated humid air, referred to as active air (containing only peroxide and hydroxyl radicals) into a liquid (see U.S. Pat. No. 5,765,403); dissolved oxygen and or photoabsorbers (metals/cations) are irradiated in the liquid being treated; combining ozone and hydrogen peroxide in water to create free radicals (U.S. Pat. No. 5,634,537); dissolved ozone and hydrogen peroxide irradiated with UV light (U.S. Pat. No. 4,849,114); laser disinfection of fluids (U.S. Pat. Nos. 4,816,145; 4,265,747)

Surface decontamination systems include a wand which sprays (using a nozzle) ozone combined with water vapor and hydrogen peroxide onto surfaces which are irradiated by a UV source (either a lamp or a fiber optic cable) on the tip of the wand (see U.S. Pat. No. 6,630,105); a reaction chamber in which the object being treated is heated on a sample stage while being irradiated from above with a UV lamp in an ozone atmosphere; sterilization of an object by exposure to an activated gas medium, composed of irradiated SF6, H2O, O2, H2S, CO, C2H2, Hg, NO, Cl2, N2O, C2H6 or mixtures thereof. (U.S. Pat. No. 5,512,244); ultrasonic nebulization of antiseptic solution (U.S. Pat. No. 5,449,502); and wound treatment with ultrasonic atomization of liquid and laser light (U.S. Pat. No. 6,761,729). A spray device which is based on ICP-MS nebulizer technology also exists for the misting of surfaces with various liquids and gases (U.S. Pat. No. 6,848,633).

Gas purification systems include a method of removing pollutants from flue gas by ozonation of the gas, followed by wet scrubbing, followed by ultra-violet radiation (see U.S. Pat. No. 6,761,863); in this invention, $NO_x$, $SO_x$, and Hg are oxidized by ozone and UV radiation to water soluble species which are removed from the gas phase into the liquid phase. The concentric nebulization of ozone with water is also patent pending for the disinfection of surfaces and treatment of gaseous odors (2004/0096354 A1). Pressurization systems in prior art allow for greater mass transfer of gas into liquids (see U.S. Pat. No. 5,971,368).

Prior art also involves catalysts which can be employed for photolytic production of hydroxyl radicals (see U.S. Pat. No. 6,866,755) include titanium dioxide ($TiO_2$), tungsten oxide ($WO_3$), zinc oxide (ZnO) and other semiconductor catalysts which produce electron hole pairs when irradiated with ultraviolet or ionizing energy; catalysts which generally speed up reaction rates are also applicable.

The method of treatment of media with nebulized oxidant combined with a radiation or energy field and catalyst is unique to the present invention. This new method is designed for superior treatment efficiency due to increased surface area for reaction between oxidants, radiation and constituent requiring oxidation leading to overall more rapid treatment time; it is also a convenient method of generating reactive oxidants for immediate application to a surface without damaging or weakening the surface with direct application of radiation or energy.

The following above-discussed US patents are listed in the following table, each patent hereby incorporated herein by reference:

TABLE

| Pat. No. | TITLE | ISSUE DATE |
|---|---|---|
| 4,265,747 | Disinfection and purification of fluids using focused laser radiation | May 19, 1981 |
| 4,267,976 | Apparatus for vaporizing and atomizing liquids | May 19, 1981 |
| 4,344,574 | Cross-flow nebulizer | Aug. 17, 1981 |
| 4,575,609 | Concentric micro-nebulizer for direct sample insertion | Mar. 11, 1986 |
| 4,696,719 | Monomer atomizer for vaporization | Sept. 29, 1987 |
| 4,816,145 | Laser disinfection of fluids | Mar. 28, 1989 |
| 4,849,114 | Oxidation of toxic compounds in water | Jul. 18, 1989 |
| 4,961,885 | Ultrasonic nebulizer | Oct. 9, 1990 |
| 4,993,411 | Ultrasonic oxygen humidifier | Feb. 19, 1991 |
| 5,213,759 | Sterilization | May 25, 1993 |
| 5,269,461 | Aerosol nozzle system | Dec. 14, 1993 |
| 5,364,537 | Process for the oxidation of organic micropollutants in water using the $O_3/H_2O_2$ combination | Nov. 15, 1994 |
| 5,366,696 | Oxygenation apparatus for oxygenating a carrier liquid by spraying | Nov. 22, 1994 |
| 5,407,604 | Humidifier using a neubilizer | Apr. 18, 1995 |
| 5,449,502 | Sterilizing apparatus utilizing ultrasonic vibration | Sep. 12, 1995 |
| 5,512,244 | Gas sterilization | Apr. 30, 1996 |
| 5,688,378 | Photoassisted oxidation of species in solution | Nov. 18, 1997 |
| 5,727,541 | Atomization of liquids | Mar. 17, 1998 |
| 5,765,403 | Water treatment method and apparatus | Jun. 16, 1998 |
| 5,884,846 | Pneumatic concentric nebulizer with adjustable and capillaries | Mar. 23, 1999 |
| 5,922,247 | Ultrasonic device for atomizing liquids | Jul. 13, 1999 |
| 5,971,368 | System to increase the quantity of dissolved gas in a liquid and to maintain the increased quantity of dissolved gas in the liquid until utilized | Oct. 26, 1999 |
| 6,009,869 | Supersonic nozzle nebulizer | Jan. 4, 2000 |
| 6,032,876 | Apparatus for forming liquid droplets having a mechanically fixed inner microtube | Mar. 7, 2000 |
| 6,030,526 | Water treatment and purification | Feb. 29, 2000 |
| 6,126,486 | Oscillating capillary nebulizer with electrospray | Oct. 3, 2000 |
| 6,166,379 | Direct injection high efficiency nebulizer for analytical spectrometry | Dec. 26, 2000 |
| 6,200,466 | Decontamination of water by photolytic oxidation/reduction utilizing near blackbody radiation | Mar. 13, 2001 |
| 6,264,899 | Method and apparatus for using hydroxyl to reduce pollutants in the exhaust gases from the combustion of a fuel | Jul. 24, 2001 |
| 6,328,898 | Method of and apparatus for forming highly oxidative water | Dec. 11, 2001 |
| 6,361,697 | Decontamination reactor system and method of using same | Mar. 26, 2002 |
| 6,468,433 | Method for disinfecting liquids and gases and devices for use thereof | Oct. 22, 2002 |
| 6,478,238 | Miniaturized fluid transfer device | Nov. 12, 2002 |
| 6,511,050 | Humidifier | Jan. 28, 2003 |
| 6,555,011 | Method for disinfecting and purifying liquids and gasses | Apr. 29, 2003 |
| 6,555,835 | Ultraviolet-ozone oxidation system and method | Apr. 29, 2003 |
| 6,630,105 | Method and apparatus for the gas phase decontamination of chemical and biological agents | Oct. 7, 2003 |
| 6,601,776 | Liquid atomization methods and devices | Aug. 5, 2003 |
| 6,761,729 | Wound treatment method and device with combination of ultrasound and laser energy | Jul. 13, 2004 |
| 6,761,863 | Process for the removal of impurities from gas streams | Jul. 13, 2004 |
| 6,780,306 | Electrionic water disinfection apparatus | Aug. 24, 2004 |
| 6,848,633 | Spray device | Feb. 1, 2005 |
| 6,866,755 | Photolytic artificial lung | Mar. 15, 2005 |
| 20040096354 | Ozone deodorizing and sterilizing method and device | May 20, 2004 |
| EP0430904 | Process for treating waste water with high concentration ozone water | Nov. 9, 1990 |

BRIEF SUMMARY OF THE INVENTION

The method of the present invention involves combining an oxidant into a liquid solution or gas through nebulization or atomization. This dispersion process also promotes interaction of the gaseous and liquid molecules which promotes oxidation reactions. The oxidant may itself be a liquid or a gas. When the oxidant is a liquid, it can be delivered undiluted or combined with a solvent or combined with the liquid to be treated. When the oxidant is a gas, it is used by itself or can be combined with the gas to be treated as the carrier gas for nebulization or atomization. As used herein, nebulizing and atomizing are interchangeable, each being defined as a process that includes the mechanical, electrical (e.g. electrospray, see http://www.newobjective.com/electrospray/index.html) or ultrasonic subdivision of a liquid to produce drops or droplets. The oxidant gas or oxidant/polluted gas mixture may then be nebulized with a liquid into the radiation field.

Ultraviolet or ionizing radiation is used to initiate reactions which form highly reactive oxidant species, such as free radicals (OH.); the radiation itself will also decompose some organic species (dependent on bond dissociation energies) but the combination of radiation and chemical oxidation as an advanced oxidation process will decompose all organics as well as oxidize metals and kill microorganisms. The frequency of energy used must be chosen based on the absorption requirements of the employed oxidant. For example, ozone is effectively decomposed into singlet oxygen by electromagnetic radiation with a wavelength less than approximately 300 nm and water is decomposed into hydroxyl radicals at a wavelength less than approximately 190 nm. Gamma rays (wavelengths less than approximately 0.1 nm) are already present when waste being treated is radioactive so the natural energy source within the waste may be incorporated into the design. All gamma radiation induces hydroxyl radical formation in water and also decomposes organics. Sonic energy induces hydroxyl radical formation through cavitation.

The method of the present invention may also be used to carry out a reduction instead of an oxidation reaction. In such a case, the invention can include a method of treating a fluid stream comprising the steps of: providing a nebulizer having a liquid inlet and a gas inlet that each communicate with an outlet; transmitting an influent fluid stream to the liquid inlet; transmitting an influent carrier gas stream to the gas inlet; using the gas stream to atomize the fluid that is emitted by the outlet, forming small droplets downstream of the outlet; and treating the atomized fluid of step "d" with a radiation field, wherein a constituent is reduced instead of oxidized.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
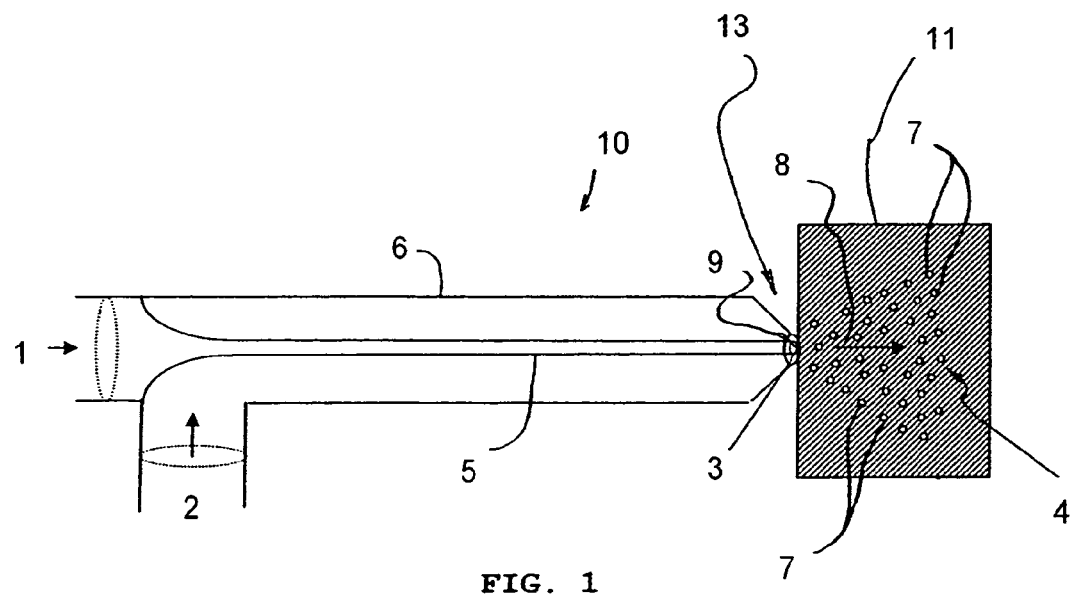
FIG. 1 is a partial perspective view of the preferred embodiment of the apparatus of the present invention illustrating the nebulizer portion thereof and the method with the distal outlet of the nebulizer is inserted into the energy field.

An example of a nebulizer 10 which can be used to combine liquid and gas is shown in FIG. 1. This device 10 can be a commercially available concentric nebulizer. The types of nebulizers which can be employed in the present invention are not limited to that pictured in FIG. 1, but can be any kind of nebulizer which atomizes a liquid through the action of a carrier gas, an applied voltage or ultrasonic waves.

Nebulizer 10 provides a pair of inlets 1, 2. Inlet 1 is a flow inlet that is used to introduce a liquid to be nebulized. The inlet 2 is an inlet for introducing a carrier gas. A liquid discharge orifice 3 and a gas discharge orifice 9 is provided at distal end portion 13 of nebulizer 10 opposite the flow inlets 1, 2 as shown in FIG. 1. During use, the nebulizer 10 uses a carrier gas injected at inlet 1 transmitted via conduit 5 to orifice 9. The liquid to be nebulized is introduced at inlet 2 and travels through conduit 6 until it reaches orifice 9. The conduits 5, 6 can be concentric as shown in FIG. 1. The orifices 3, 9 can also be concentric.

Figure 2:
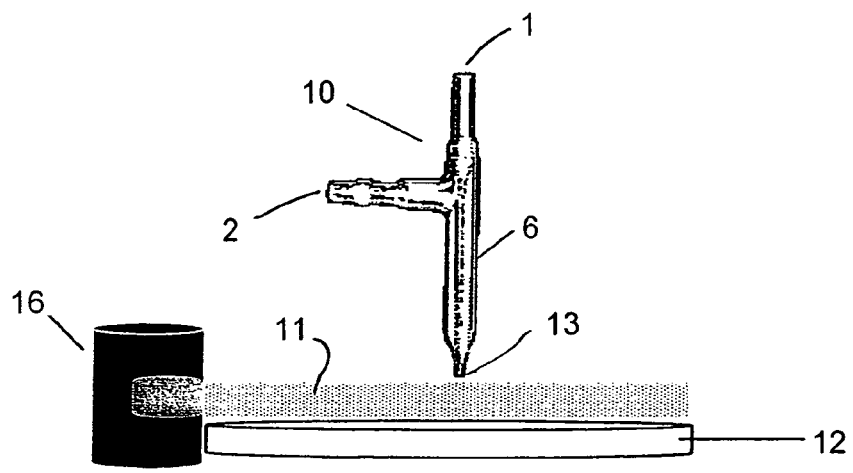
FIG. 2 is a schematic diagram of the preferred embodiment of the apparatus of the present invention and of the method showing a nebulized cloud injected through an energy field onto a surface.

A nebulized cloud 4 is discharged as indicated by arrow 8 in FIG. 1. The nebulized cloud 4 can be injected through an energy field 11 onto a surface 12, as shown in FIG. 2.

Figure 3:
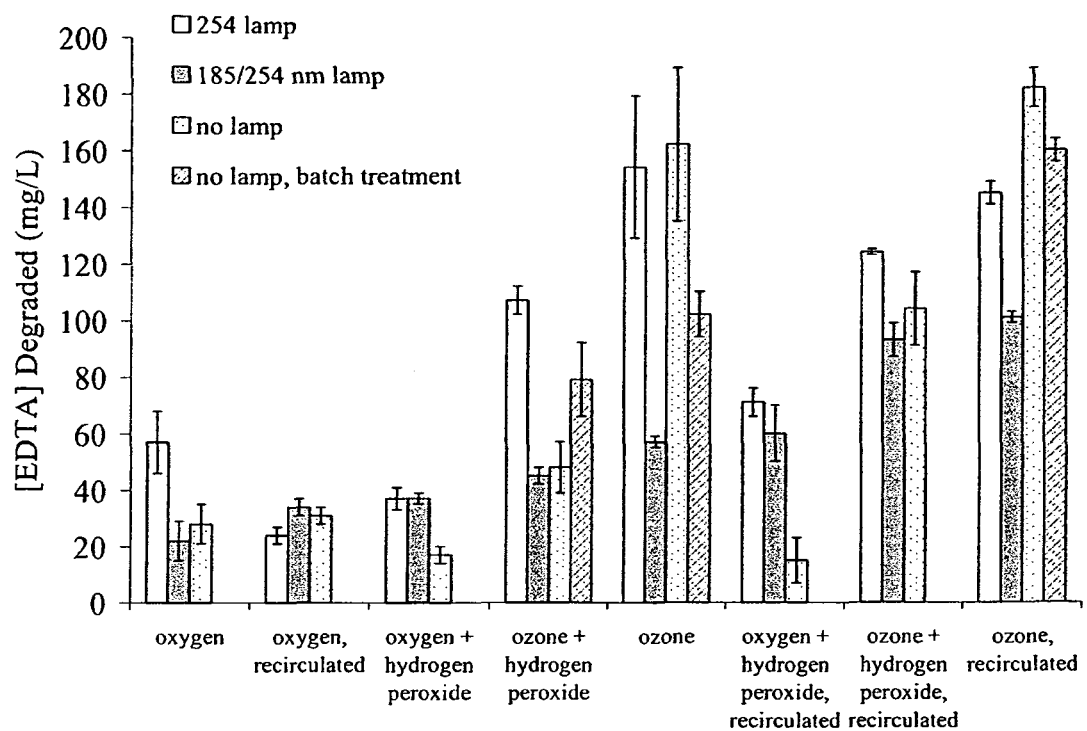
FIG. 3 is a graphical representation of the treatment of EDTA solution by nebulized hydrogen peroxide and/or ozone.
Figure 4:
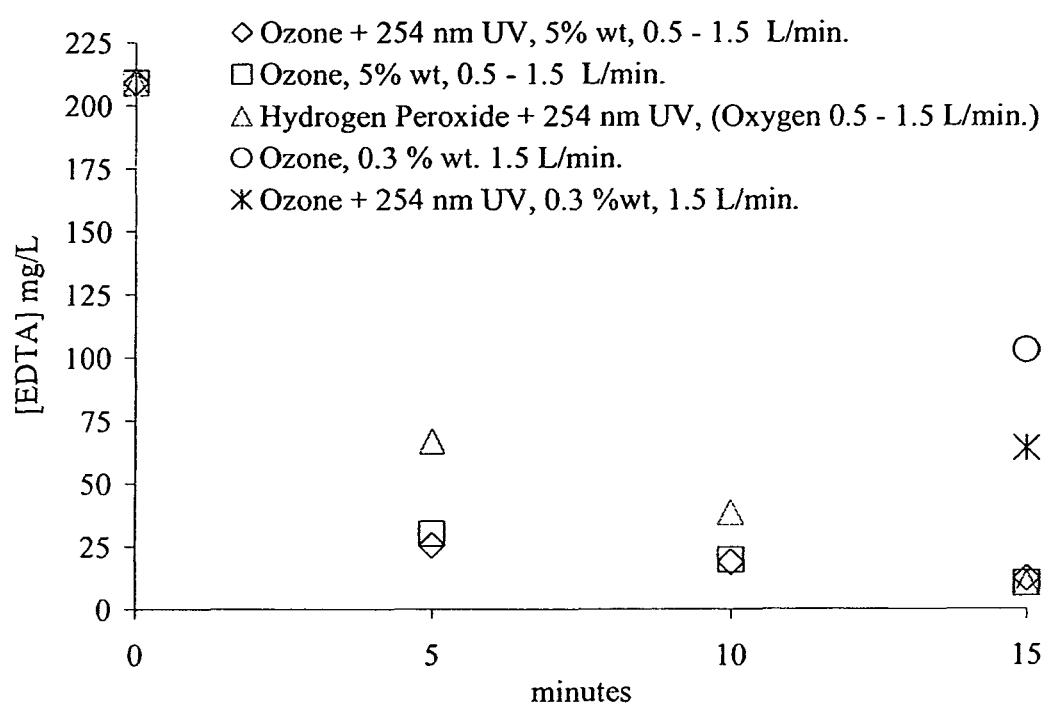
FIG. 4 is a graphical representation of the treatment of EDTA solution by nebulized hydrogen peroxide and/or ozone.

The treatment of EDTA solution by nebulized hydrogen peroxide and or ozone in a 254 nm or combined 185/254 nm UV radiation field is shown in FIGS. 3 and 4.

Figure 5:
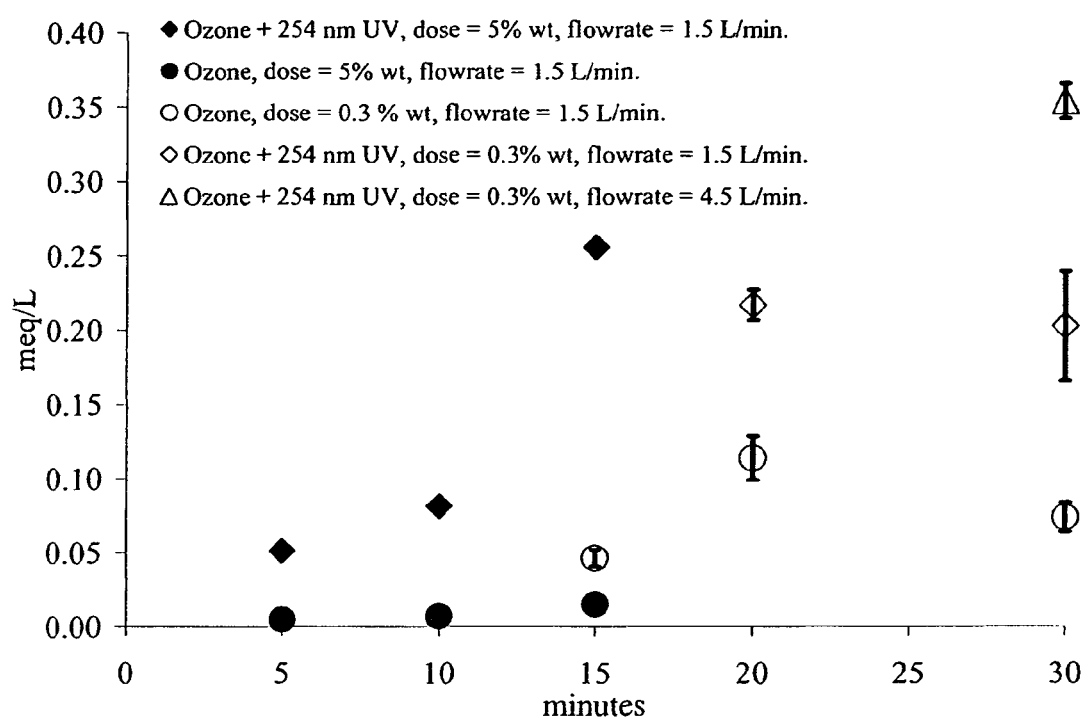
FIG. 5 is a graphical representation showing the oxidation of CR(III) to CR(VI) by nebulized ozone in a UV radiation field.

The oxidation of Cr(III) to Cr(VI) by nebulized ozone in a 254 nm UV radiation field is shown in FIG. 5.

FIG. 3 shows degradation of EDTA in screening experiments to test the effectiveness of nebulized $O_3$, $O_2$, $H_2O_2$ and different UV lamps in plug flow and batch treatment. Experimental conditions: $[EDTA]_i$=200 or 400 mg/L, pH uncontrolled (pH=5.77±0.6), T=20.6±0.5° C.

FIG. 4 shows a comparison of nebulized $O_3$, nebulized $O_3$+254 nm UV, and nebulized $H_2O_2$+254 nm UV oxidation of EDTA during recirculating batch experiments. Experimental conditions: $[EDTA]_i$~210 mg/L, pH uncontrolled (pH=7.1±0.6), T=21.2±1.9° C.

FIG. 5 shows milliequivalents of electrons transferred during oxidation of Cr(III). Experimental Conditions: $[Cr^{3+}]$=90 mg/L for all except $\alpha$, where $[Cr^{3+}]$=10 mg/L), pH uncontrolled (pH=3.96±0.53), T=22.3±1.5° C.

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

EXAMPLE 1

This example illustrates the mechanism by which a liquid is treated. The liquid requiring treatment may be blended with another liquid (a solvent or oxidant chosen based on the application of the method) and is pumped through the inner capillary tube through the liquid inlet 1 of the nebulizer. A carrier gas, which may also be an oxidant, is routed through the gas inlet 2 of the nebulizer. The liquid requiring treatment is atomized into small droplets by the carrier gas at the tip of the nebulizer 3. The liquid droplets and gas are injected into an energy field 4; the tip of the nebulizer may also be coated with a photocatalyst which, when inserted into a ultraviolet or ionizing radiation field will promote oxidation reactions. The liquid and/or gas oxidant as well as any nanoparticulate photocatalyst added to the liquid or gas will be energized by the field to form excited species, such as free radicals, which are more powerful oxidants than the parent compound. Gas oxidants will oxidize the contaminants in the liquid at the surface of the droplets and liquid oxidants will oxidize the contaminants inside the droplets. Dose of the oxidants must be designed based on the concentration of contaminant.

Examples of gaseous oxidants which may be used as parent compounds to form reactive gas or dissolved species include but are not limited to:
1. Ozone ($O_3$) which forms singlet oxygen $O^1D$ upon excitation
2. Nitrogen Dioxide, $NO_2$, which dissolves into water as nitric acid $HNO_3$ and becomes peroxynitrous acid (HO-NOO) upon excitation.

Examples of liquid oxidants which may be used as parent compounds to form reactive dissolved species include but are not limited to:

1. Hydrogen peroxide ($H_2O_2$) which splits into 2 hydroxyl radicals (OH.) upon excitation
2. Persulfate ($S_2O_8$) which forms sulfate radicals ($SO_3^-$.) upon excitation Examples of catalysts which may be used to promote oxidation reactions include but are not limited to:
1. Titanium dioxide ($TiO_2$)
2. Tungsten oxide ($WO_3$)
3. Zinc Oxide (ZnO)
4. Tantalum and Nickel Oxides Cocatalyst Examples of the energy field which may be used to promote reactive species formation include but are not limited to:
1. Ultraviolet radiation (UV)
2. Sonication
3. X-Rays
4. Gamma Rays
5. Microwaves

EXAMPLE 2

This example illustrates the mechanism by which a contaminated gas is treated. The gas requiring treatment may be blended with another gas before being routed through the gas inlet 2 of the nebulizer. A liquid solvent and/or oxidant, chosen based on the application of the method, is pumped through the inner capillary tube through the liquid inlet 1 of the nebulizer. Liquid droplets are formed from the velocity of the gas at the tip of the nebulizer 3 and both are injected into the energy field 4. Particulates and volatile organic or inorganic species in the gas requiring treatment may be scrubbed in the nebulized liquid droplets before or after oxidation to soluble species. Oxidation may occur in the gas phase by the direct action of the energy field, or by excited species formed in the gas, or may occur in the liquid phase. Gaseous organic species may also be mineralized to carbon dioxide ($CO_2$) by oxidants at the surface of the liquid. Dose of the oxidants can be designed based on the concentration of contaminant.

The examples of gas and liquid oxidants as well as energy fields and catalysts described in Example 1 are also applicable in this example.

This embodiment can be specifically employed in devices for the purification and decontamination of air in rooms or within ventilation systems.

EXAMPLE 3

A gas and liquid are simultaneously treated. The combined methods described in examples 1 and 2 are simultaneously employed to treat a contaminated gas and a contaminated liquid.

This embodiment can be specifically employed in a compact device for the simultaneous treatment of drinking water and indoor air.

EXAMPLE 4

A surface 12 is treated by the nebulized excited mist/cloud 11. A liquid oxidant and/or solvent is pumped through the inner capillary tube or conduit 5 via liquid inlet 1 of the nebulizer 10 (see arrow 14). A carrier gas, which may also be an oxidant, is routed through the gas inlet 2 of the nebulizer 10 (see arrow 15). The liquid is atomized into small droplets 7 by the carrier gas at the distal tip 13 of the nebulizer 10 and are injected with the gas into an energy field 11. The energy field 11 can be produced from a collimating source 16 so that the energy field 11 is parallel to but not touching the surface 8.

The following is a list of parts and materials suitable for use in the present invention.

PARTS LIST

Part Number Description

1 liquid inlet
2 gas inlet
3 liquid outlet orifice
4 nebulized cloud
5 capillary tube/liquid conduit
6 gas conduit
7 droplet
8 arrow
9 gas outlet orifice
10 nebulizer
11 energy field
12 surface
13 distal tip
14 arrow
15 arrow All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A method of treating a waste stream comprising the steps of:
   a) providing a nebulizer having a liquid inlet, a gas inlet, and an outlet for emitting atomized fluid;
   b) transmitting a liquid stream to the liquid inlet;
   c) transmitting a gas stream to the gas inlet;
   d) using the gas stream and/or an applied voltage and/or ultrasonic waves to break up the liquid stream into droplets;
   e) discharging the droplets and gas from the outlet as an atomized fluid mixture;
   f) irradiating the atomized fluid mixture; and
   g) wherein in steps "e" and "f" the atomized fluid mixture includes a waste material to be treated; and
   h) wherein the waste material is treated with irradiation in step "f",
   further comprising the step of adding a catalyst to at least part of the surface of the nebulizer to enhance reactive species production.

2. The method of claim 1 further comprising the step of adding a catalyst to at least part of the surface of the nebulizer to enhance hydroxyl radical production.

3. A method of treating a waste stream comprising the steps of:
   a) providing a nebulizer having a liquid inlet, a gas inlet, and an outlet for emitting atomized fluid;
   b) transmitting a liquid stream to the liquid inlet;
   c) transmitting a gas stream to the gas inlet;
   d) using the gas stream and/or an applied voltage and/or ultrasonic waves to break up the liquid stream into droplets;
   e) discharging the droplets and gas from the outlet as an atomized fluid mixture;
   f) irradiating the atomized fluid mixture; and
   g) wherein in steps "e" and "f" the atomized fluid mixture includes a waste material to be treated; and h) wherein the waste material is treated with irradiation in step "f", further comprising the step of adding a catalyst to at least part of the surface of the nebulizer to enhance hydroxyl radical production.

4. The method of claim 3 wherein the catalyst is added to the surface of the nebulizer next to the outlet.

5. A method of treating a waste water stream comprising the steps of:

a) providing a nebulizer having a liquid inlet and a gas inlet that each communicate with an outlet;

b) transmitting an influent waste water flow stream to the liquid inlet;

c) transmitting an influent carrier gas stream to the gas inlet;

d) using the gas stream to atomize the fluid that is emitted by the outlet, forming small droplets downstream of the outlet; and e) treating the atomized fluid of step "d" with a radiation field, wherein a constituent is reduced instead of oxidized.

6. The method of claim 5 wherein oxidation reduction reactions take place on the surface of the droplets in steps "d" and "e".

7. A method of treating a fluid stream comprising the steps of:

a) providing a nebulizer having a liquid inlet, a gas inlet, and an outlet for emitting atomized fluid;

b) transmitting a fluid stream to the liquid inlet;

c) transmitting a gas stream to the gas inlet;

d) using the gas stream and/or an applied voltage and/or ultrasonic waves to break up the fluid stream into droplets;

e) discharging the droplets and gas from the outlet as an atomized fluid mixture;

f) irradiating the atomized fluid mixture; and g) wherein in steps "e" and "f" the atomized fluid mixture includes a material to be treated; and h) wherein the material is treated with irradiation in step "f", further comprising the step of adding a catalyst to at least part of the surface of the nebulizer.

8. The method of claim 7, wherein the catalyst enhances hydroxyl radical production.

9. A method of treating a fluid stream comprising the steps of:

a) providing a nebulizer having a liquid inlet and a gas inlet that each communicate with an outlet;

b) transmitting an influent fluid flow stream to the liquid inlet;

c) transmitting an influent carrier gas stream to the gas inlet;

d) using the gas stream to atomize the fluid that is emitted by the outlet, forming small droplets downstream of the outlet; and e) treating the atomized fluid of step "d" with a radiation field, wherein a constituent is reduced instead of oxidized.

10. A method of treating a fluid stream comprising the steps of:

a) providing a nebulizer having a liquid inlet and a gas inlet that each communicate with an outlet;

b) transmitting an influent fluid flow stream to the liquid inlet;

c) transmitting an influent carrier gas stream to the gas inlet, wherein the gas stream includes any gas that is an oxidant;

d) using the gas stream to atomize the fluid that is emitted by the outlet, forming small droplets downstream of the outlet;

e) treating the atomized fluid of step "d" with a radiation field; and f) wherein the oxidant gas is ozone.

11. A method of treating a fluid stream comprising the steps of:

a) providing a nebulizer having a liquid inlet and a gas inlet that each communicate with an outlet;

b) transmitting an influent fluid flow stream to the liquid inlet;

c) transmitting an influent carrier gas stream to the gas inlet, wherein the gas stream includes any gas that is an oxidant;

d) using the gas stream to atomize the fluid that is emitted by the outlet, forming small droplets downstream of the outlet;

e) treating the atomized fluid of step "d" with a radiation field; and f) wherein the oxidant gas is nitrogen dioxide.

* * * * *